United States Patent
Candidus et al.

(10) Patent No.: US 10,111,605 B2
(45) Date of Patent: Oct. 30, 2018

(54) POSITIONING CUSHION FOR A MEDICAL IMAGING EXAMINATION, AND MEDICAL IMAGING APPARATUS WITH A POSITIONING CUSHION

(71) Applicant: Siemens Healthcare GmbH, Erlangen (DE)

(72) Inventors: Yvonne Candidus, Fuerth (DE); Daniel Driemel, Oederan (DE); Lukas Endner, Bayreuth (DE); Hubertus Fischer, Bamberg (DE); Wolfgang Kraus, Fuerth (DE); Thomas Kundner, Buckenhof (DE); Martin Zigann, Moehrendorf (DE); Stephan Zink, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 190 days.

(21) Appl. No.: 15/185,715

(22) Filed: Jun. 17, 2016

(65) Prior Publication Data

US 2016/0367167 A1 Dec. 22, 2016

(30) Foreign Application Priority Data

Jun. 17, 2015 (DE) ......................... 10 2015 211 112

(51) Int. Cl.
*A61G 7/065* (2006.01)
*A61B 5/055* (2006.01)
*A61B 5/00* (2006.01)
*G01R 33/30* (2006.01)

(52) U.S. Cl.
CPC ............ *A61B 5/0555* (2013.01); *A61B 5/704* (2013.01); *G01R 33/30* (2013.01)

(58) Field of Classification Search
CPC ................................ A61B 5/065; A61G 7/065
USPC .................................... 5/621–624, 632, 640
See application file for complete search history.

(56) References Cited

U.S. PATENT DOCUMENTS

| | | | |
|---|---|---|---|
| 5,142,720 A * | 9/1992 | Kelso | ..................... A61G 7/001 5/630 |
| 2011/0087142 A1 | 4/2011 | Ravikumar et al. | |
| 2012/0264997 A1* | 10/2012 | Isham | .................. A61G 13/123 600/1 |
| 2013/0283526 A1 | 10/2013 | Gagliardi | |

FOREIGN PATENT DOCUMENTS

WO WO-2012076199 A1 6/2012
WO WO-2013182348 A1 12/2013

* cited by examiner

*Primary Examiner* — Fredrick C Conley
(74) *Attorney, Agent, or Firm* — Schiff Hardin LLP

(57) ABSTRACT

A positioning cushion for patient undergoing an imaging procedure in a medical imaging apparatus, with a first positioning unit that has a foam material and a second positioning unit, wherein the second positioning unit has at least one fluid cushion able to be filled with a fluid.

10 Claims, 5 Drawing Sheets

POSITIONING CUSHION FOR A MEDICAL IMAGING EXAMINATION, AND MEDICAL IMAGING APPARATUS WITH A POSITIONING CUSHION

BACKGROUND OF THE INVENTION

Field of the Invention

The present invention concerns a positioning cushion of the type having a first positioning unit, which has a foam material, and a second positioning unit. Furthermore the present invention concerns a medical imaging apparatus with such a positioning cushion.

Description of the Prior Art

During a medical imaging examination, especially a magnetic resonance examination, it is important for the patient being examined to remain as motionless as possible. To achieve this, attempts are made to positionally fix at least the areas of the patient to be examined, so that even unintentional movements of the patient can be prevented where possible.

SUMMARY OF THE INVENTION

An object of the present invention is to achieve positioning and/or fixing of a patient in an imaging apparatus that is particularly simple and saves time during preparation of the medical imaging examination.

The invention is based on a positioning cushion with a first positioning unit, which includes a foam material, and a second positioning unit.

In accordance with the invention, the second positioning unit has at least one fluid cushion that is selectively fellable only with a fluid (i.e., there is no substance other than fluid in the second positioning unit).

In this context a fluid means a gaseous and/or a liquid substance, by which the at least one fluid cushion of the second positioning unit is able to be filled selectively at the site of use (i.e., other than at a manufacturing site). The fluid can be any fluid that is reasonable to those skilled in the art. Preferably, however the fluid is air, so that a particularly cost-effective and readily-available fluid can be provided for filling the at least one fluid cushion. Furthermore, the fluid cushion is to be understood as a container able to be closed off from the outside and variable in its shape, in which a fluid can be enclosed.

As used herein, a foam material means an elastic material with a cellular structure, wherein a gas, especially air, is enclosed in the individual cells.

This invention allows a particularly simple positioning and/or fixing of the patient on a patient support for a medical imaging examination, since the patient can be supported in a stable manner by the fillable positioning cushion. A simple positioning of areas of the patient, especially of areas of the patient to be examined, can be achieved by the positioning cushion, within a local radio-frequency antenna unit for example, without a movement of the area of the patient to be examined being possible within the local radio-frequency antenna unit during the medical imaging examination, such as a magnetic resonance examination. Here a space between the area of the patient to be examined and the local radio-frequency antenna unit is preferably filled by the positioning cushion. The positioning cushion can be put into position in an emptied state and then filled with the fluid thereafter. Furthermore with the positioning cushion, especially with the fillable fluid cushion, a versatile use of the positioning cushion is possible, since by only partially filling the fluid cushion and/or a partially emptying the fluid cushion, the shape and/or an extent of the positioning cushion can be adapted to an application and/or a situation. Depending on the embodiment of the second positioning unit, this unit can have a single fluid cushion, or two or more fluid cushions.

Preferably there is also damping, by the foam material, of mechanical vibrations that could be transmitted from the medical imaging apparatus to the patient. This can contribute to making the patient more comfortable during the medical imaging examination. It also can lead to a reduction in the noise to which the patient is subjected.

In an embodiment, the second positioning unit has a valve opening for filling or emptying the at least one fluid cushion. This allows a simple and rapid filling and/or emptying of the at least one fluid cushion, especially during a preparation of a medical imaging examination. In addition, the positioning cushion can be adapted particularly easily to the space available for the positioning cushion, for example between the patient and the patient couch and/or local radio-frequency antenna unit.

In a further embodiment of the invention, the first positioning unit has a first surrounding frame and for the second positioning unit to have a second surrounding frame, wherein the first and the second surrounding frames are connected to one another. This achieves a stable connection with, at the same time, a volume of the positioning cushion embodied so as to be able to be varied. Preferably, the first surrounding frame and the second surrounding frame are connected to each another by thermal molding and/or are welded to each another, so that the fluid cushion is also fluid-tight against one surrounding frame. Preferably the valve opening of the second positioning unit is also disposed in an area of the surrounding frame.

The second positioning unit can have at least one preshaped envelope, so a maximum volume of the positioning cushion, particularly of the second positioning unit, can be obtained in a simple manner. In addition, the positioning unit can be adapted to specific requirements, such as knee examinations, for which the positioning cushion rests against a patient's knee. In particular, the envelope of the second positioning unit can be adapted to requirements of the medical imaging apparatus, such as with respect to hygiene and/or sterility, etc.

In a further embodiment, the second positioning unit has an emptied state and at least one envelope of the second positioning unit assumes a predefined position in the emptied state. In this way a simple cleaning of the at least one emptied fluid cushion and/or a simple emptying of the fluid cushion can be achieved. Also, a simple removal of the positioning cushion after a medical imaging examination can be achieved since, to do this, the fluid cushion is merely emptied and subsequently the positioning cushion can be removed. The effort of folding the positioning cushion and/or the fluid cushion thus is not needed. Furthermore, this makes the positioning cushion immediately ready for use again after emptying, so as to be available for its next application. Because of the pre-defined position in the emptied state, in this emptied state an especially flat construction can be achieved, so that the positioning cushion can be positioned simply to support the patient correctly.

In a further embodiment of the invention, the first positioning unit has at least one foam cushion, wherein the at least one foam cushion has at least one recess. This enables a positioning cushion to be provided in which individual areas can exhibit different pressure characteristics when resting against a patient. In this way for example, with especially sensitive and/or painful areas of the patient's body, the area of the positioning cushion that has the at least one recess can rest against this area of the patient's body, so that greater comfort and/or a feeling of wellbeing can be achieved for the patient. Furthermore, the positioning cushion can also be adapted for a specific application by this feature, such as for being arranged on a patient's knee for a knee examination using a local radio-frequency antenna unit. The at least one recess of the foam cushion thus allows a simple adaptation of the positioning cushion to different positions of the patient, and thus an area of application for the positioning cushion can be expanded.

As an alternative or in addition, the first positioning unit can have at least two foam cushions embodied separately from one another. In this way a simple subdivision of the positioning cushion can be achieved, so that two or more foam cushions can be available within the positioning cushion for positioning of the patient. In addition this enables an area of application to be expanded, since the multiple foam cushions allow a simple adaptation of the positioning cushion to different positions. The subdivision of the second positioning unit into two or more foam cushions can be adapted in this case to a specific application, such as a knee examination with a local radio-frequency antenna unit.

In a further embodiment of the invention, the positioning cushion has a third positioning unit, wherein the third positioning unit has a stabilization unit. This makes possible an especially stable positioning cushion, the shape of which can be predetermined in at least one direction by the stabilization unit. Due to the stabilization unit, a simple fitting of the positioning cushion, especially in areas which provide little space for the positioning of the positioning cushion, can be achieved, because the stabilization unit makes it possible for the positioning cushion to be easily pushed into the space. Preferably the stabilization unit has a stabilization plate, so that the positioning cushion can be kept especially compact.

In another embodiment of the invention, the first positioning unit has a first positioning layer, the second positioning unit has a second positioning layer, and the third positioning unit has a third positioning layer. In this way an especially effective support of the patient can be achieved, since through the three-layer construction of the positioning cushion all three layers can be effective simultaneously.

The third positioning unit can be disposed between the first positioning unit and of the second positioning unit, so that a decoupling is achieved between the first positioning unit, especially between the foam material and/or the at least one foam cushion, and the second positioning unit, especially the at least one fluid cushion. In addition, an upholstered layer, especially a fluid-upholstered layer and a foam-upholstered layer, can be disposed on both sides of the stabilization layer so that, independent of the position of the positioning cushion on the patient, a pleasant and/or soft layer is resting against the patient.

In a further embodiment of the invention, the first positioning unit has first surrounding frame, the second positioning unit has a second surrounding frame, and the third positioning unit has a third surrounding frame, and the first, second, and third surrounding frames are connected to one another. This makes possible a stable connection with, at the same time, a volume of the positioning cushion embodied so as to be able to be varied. Especially advantageously, the first, second, and third surrounding frames are connected to one another by thermal molding and/or are welded to one another, so that the fluid cushion is also fluid-tight against one surround.

The first positioning unit can have at least one foam cushion and the at least one foam cushion can at least include one sloping side surface, with the at least one fluid cushion of the second positioning unit being disposed at least partly against the at least one sloping side surface. In this way, the basic shape of the positioning cushion can be provided by the at least one foam cushion and only the side surfaces of the positioning cushion can be filled with a fluid, especially with air, for exact positioning and/or fixing of the patient. In this context, a side surface of the at least one foam cushion is to be understood as a surface that adjoins a main extent surface of the upper surface of the foam cushion. Furthermore a sloping side surface is to be understood as a side surface that encloses an obtuse angle with the main extent surface of the upper surface of the at least one foam cushion.

In a further embodiment of the invention, the first positioning unit has at least one foam cushion and the second positioning unit has at least one envelope, and the at least one foam cushion has a central outer area with the at least one envelope resting on the central outer area. In this context, a central outer area of the foam cushion is to be understood as an area of a surface of the at least one foam cushion, the area being disposed centrally and/or in the middle on one side of the surface. This embodiment of the invention enables the first positioning unit, especially the at least one foam cushion, to assume the shape of the positioning cushion in an emptied state of the second positioning unit, especially of the at least one fluid cushion. Preferably, the at least one envelope is firmly connected to the central outer area, so that a fluid-tight closure of the at least one fluid cushion can be achieved.

The invention also encompasses a medical imaging apparatus with a positioning cushion having a first positioning unit and a second positioning unit, wherein the first positioning unit has a foam material and the second positioning unit has at least one fluid cushion able to be filled with a fluid.

This medical imaging apparatus achieves an especially simple positioning and/or fixing of the patient on a patient support device for a medical imaging examination, since the patient can be supported stably by the fillable positioning cushion. In particular, with the positioning cushion, a simple positioning of areas of the patient can be achieved, especially of areas of the patient to be examined, within a local radio-frequency antenna unit, for example, without a movement of the area of the patient to be examined being possible within the local radio-frequency antenna unit during the medical imaging examination, especially a magnetic resonance examination. Here a space between the area of the patient to be examined and the local radio-frequency antenna unit is preferably filled by the positioning cushion, and the positioning cushion can be put into position in an emptied state and then filled with the fluid thereafter. Furthermore, by the positioning cushion, especially by the fillable fluid cushion, a versatile use of the positioning cushion is possible, since as a result of partial filling of the fluid cushion and/or partial emptying of the fluid cushion, the shape and/or extent of the positioning cushion can be adapted to an application and/or a situation.

The advantages of the inventive medical imaging apparatus essentially correspond to the advantages of the inventive positioning cushion, as described in detail above. Features, advantages and alternate embodiments noted above are applicable to the apparatus as well.

DESCRIPTION OF THE PREFERRED EMBODIMENTS

Figure 1:
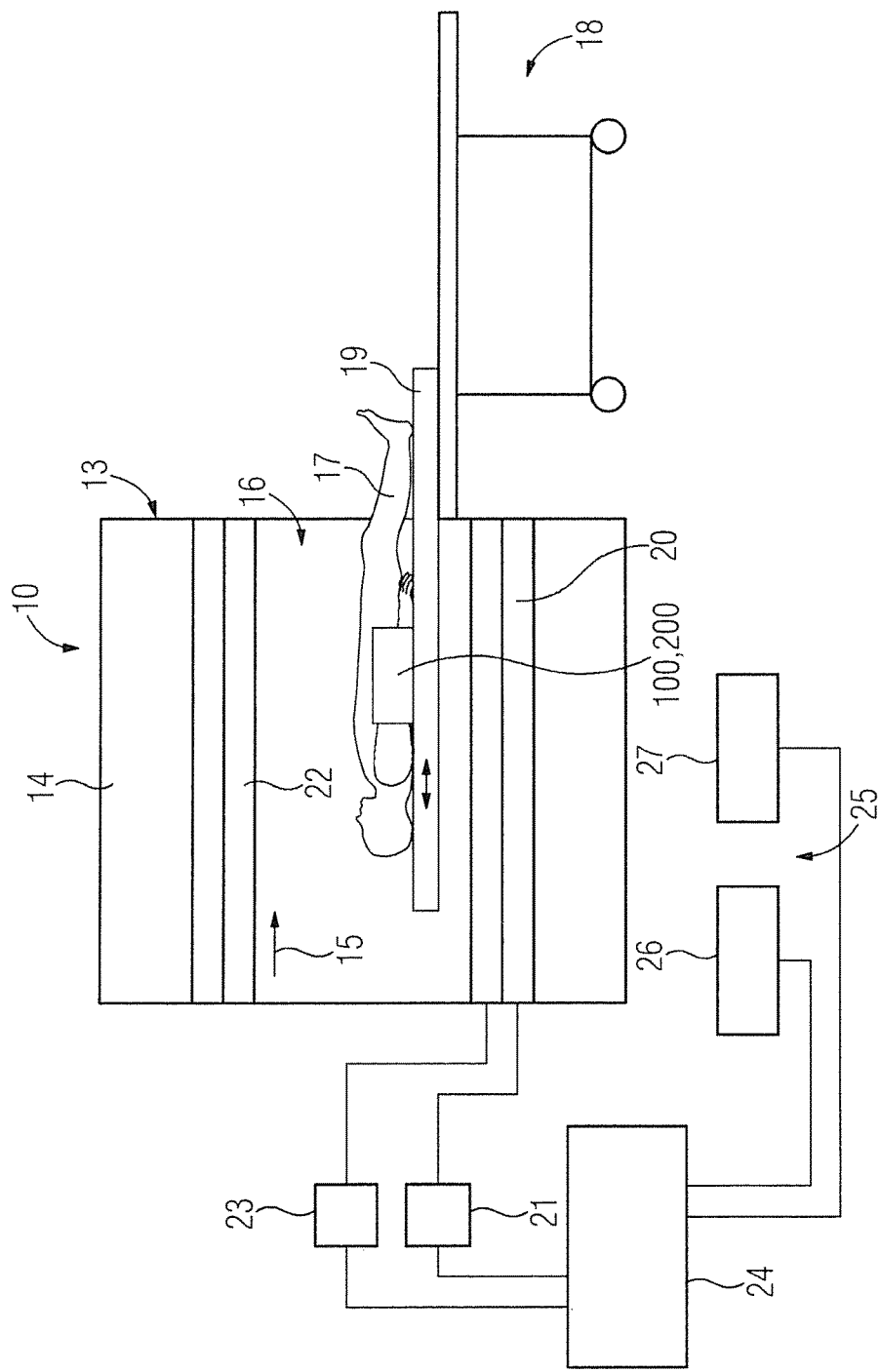
FIG. 1 shows an inventive medical imaging apparatus with a positioning cushion, in a schematic illustration.

FIG. 1 schematically illustrates a medical imaging apparatus 10. In the exemplary embodiment, the medical imaging apparatus 10 is formed as a magnetic resonance apparatus. The embodiment of the medical imaging apparatus 10, however, is not restricted to a magnetic resonance apparatus. The medical imaging apparatus 10 can be formed by any medical imaging apparatus appearing reasonable to those skilled in the art, such as a computed tomography device, a positron emission tomography device etc.

The medical imaging apparatus in the embodiment of a magnetic resonance apparatus has a scanner 13 formed by a magnet unit, which includes a superconducting basic field magnet 14 for creating a strong and constant basic magnetic field 15. The magnetic resonance scanner 13 has a patient receiving area 16 for receiving a patient 17. In the exemplary embodiment, the patient receiving area 16 has a cylindrical shape and is surrounded in a circumferential direction by the scanner 13. An embodiment of the patient receiving area 16 differing therefrom, however, is readily conceivable. The patient 17 can be moved into the patient receiving area 16 by a patient support 18 of the magnetic resonance scanner 13. To this end the patient support 18 has a patient table 19 that is movable within the patient receiving area 16.

The scanner 13 also has a gradient coil arrangement 20 for creating magnetic field gradients for spatial encoding during imaging. The gradient coil arrangement 20 is controlled by a gradient control processor 21 of the magnetic resonance apparatus. The scanner 13 also has a radio-frequency antenna 22 for exciting nuclear spins in the patient 17 so as to deviate from the polarization that arises in the basic magnetic field 15 created by the basic field magnet 14. The radio-frequency antenna 22 is controlled by a radio-frequency antenna control processor 23 so as to emit radio-frequency magnetic resonance sequences into an examination space that is essentially formed by a patient receiving area 16 of the scanner 13.

To control the basic field magnet 14, the gradient control processor 21 and the radio-frequency antenna control processor 23, the magnetic resonance apparatus has a system control computer 24. The system control computer 24 centrally controls the magnetic resonance scanner 13, such as to execute a predefined imaging gradient echo sequence. The system control computer 24 has an evaluation unit (not shown) for evaluation of medical image data acquired during the magnetic resonance examination. Furthermore the magnetic resonance scanner 13 has a user interface 25, which is connected to the system control computer 24. Control information, such as imaging parameters for example, as well as reconstructed magnetic resonance images, can be displayed on a display unit 26, for example on at least one monitor, of the user interface 25 for medical operating personnel. Furthermore the user interface 25 has an input unit 27, via which information and/or parameters can be entered during a measurement process by the medical operating personnel.

For an exact and motionless positioning and/or fixing of the patient 17, especially of the area to be examined of the body of the patient 17 on the patient table 19, the magnetic resonance scanner 13 has a positioning cushion 30. The magnetic resonance scanner 13 can have two or more positioning cushions 100, 200.

Figure 2:
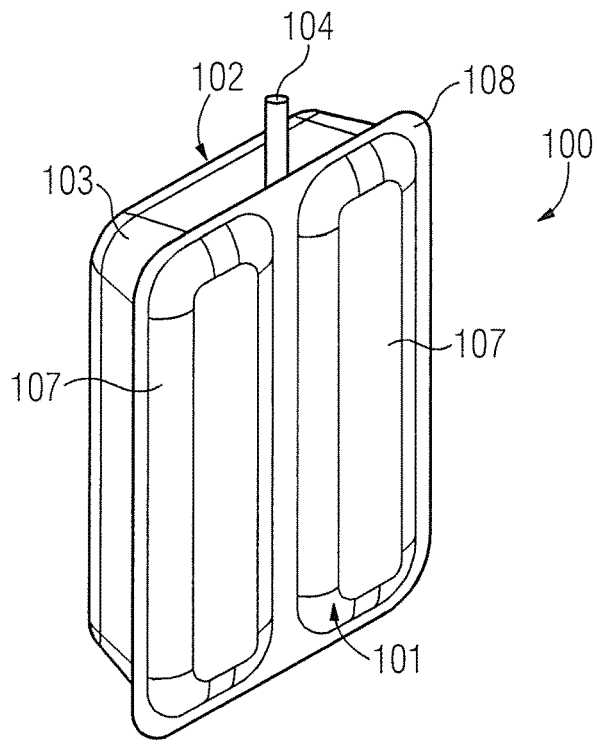
FIG. 2 shows a first exemplary embodiment of the positioning cushion, in a perspective view from the front.
Figure 3:
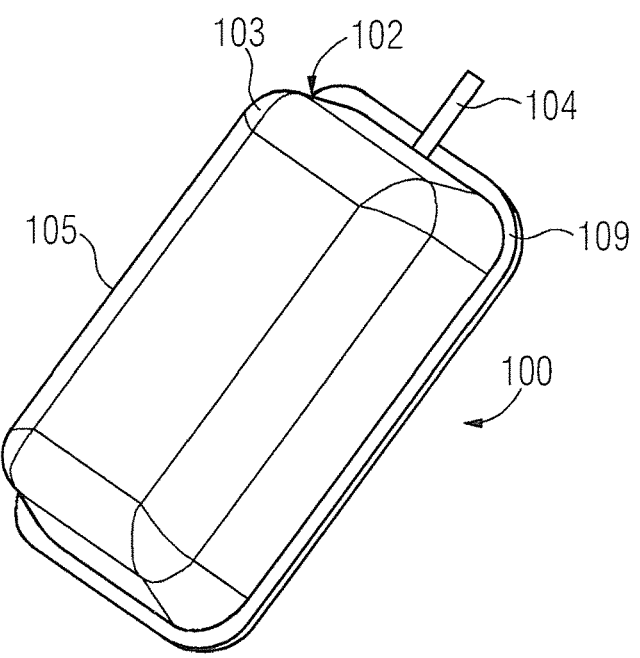
FIG. 3 shows the first exemplary embodiment of the positioning cushion, in a perspective view from the rear.
Figure 4:
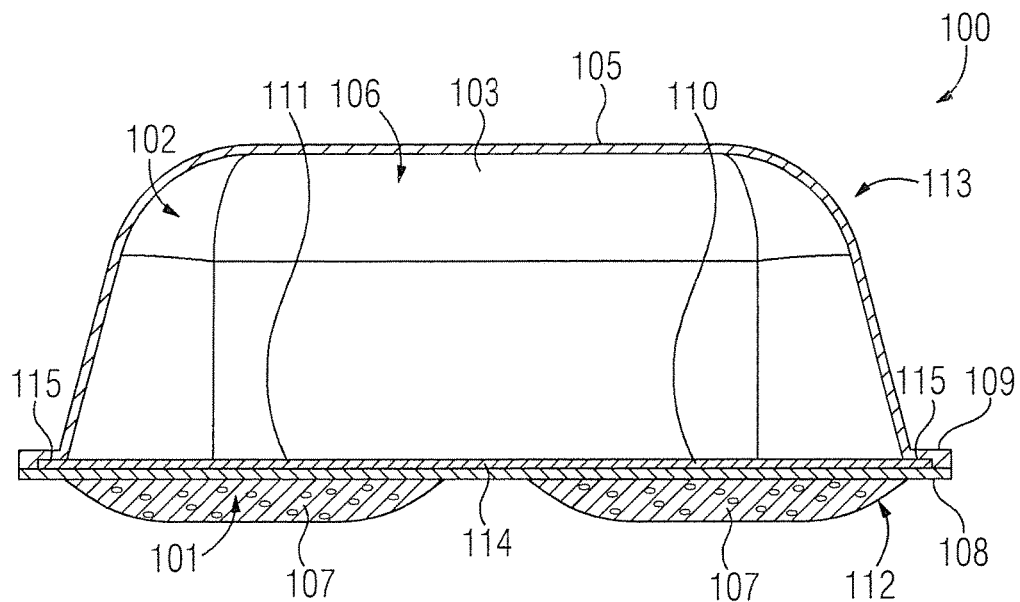
FIG. 4 shows a sectional view of the first exemplary embodiment of the positioning cushion in a filled state.
Figure 5:
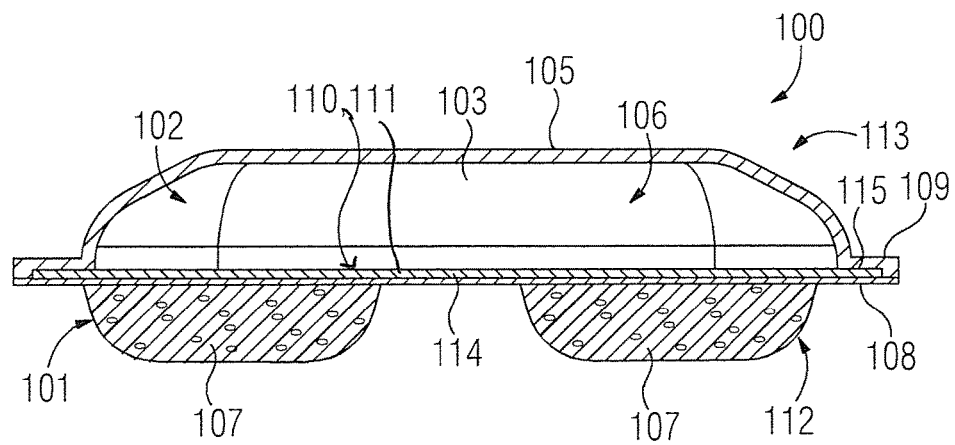
FIG. 5 shows a sectional view of the first exemplary embodiment of the positioning cushion in an emptied state.

FIGS. 2 to 5 show a first embodiment of the positioning cushion 100. The positioning cushion 100 has a first positioning unit 101 and a second positioning unit 102. The first positioning unit 101 has a foam material. The second positioning unit 102 has a fluid cushion 103 able to be filled with a fluid. In the exemplary embodiment, the second positioning unit 102 has a single fluid cushion 103. An embodiment of the second positioning unit 102 with two or more fluid cushions 103 is also readily possible (FIGS. 4 and 5).

The second positioning unit 102 has a valve opening 104 for filling the fluid cushion 103 and/or for emptying the fluid cushion 103. In the present exemplary embodiment the fluid is formed by air, so that, via the valve opening 104, the fluid cushion 103 is able to be filled with air, or air can escape through the valve opening 104 from the fluid cushion 103 (FIGS. 2 and 3). In an alternate embodiment of the invention, filling of the fluid cushion 103 with further fluids appearing reasonable to those skilled in the art is also readily conceivable.

The second positioning unit 102 further has an envelope 105 that surrounds the receiving area 106 for receiving a fluid of the fluid cushion 103. The envelope 105 is made of a fluid-tight material, so that no fluid can escape from the fluid cushion 103 through the envelope 105. Furthermore the envelope 105 is pre-shaped, so that in a filled state of the fluid cushion 103 (FIG. 4) of the second positioning unit 102, the fluid cushion 103 assumes an exactly defined position and/or extent in relation to the first positioning unit 101. In an emptied state (FIG. 5) of the fluid cushion 103 too, the pre-shaped envelope 105 assumes a defined and/or predetermined position. Between the emptied state (FIG. 5) and the filled state (FIG. 4) of the fluid cushion 103 there is an increase in volume of the positioning cushion 100 of at least 50% of the volume in the emptied state. Preferably the increase in volume amounts to at least 80% and especially advantageously to at least 100% of the volume in the emptied state.

The first positioning unit 101 has at least one foam cushion 107. In the exemplary embodiment the first positioning unit 101 has two foam cushions 107 that are embodied separately from one another (FIGS. 2, 4 and 5). In an alternate embodiment of the invention the first positioning unit 101 can also have just a single foam cushion 107 or also more than two foam cushions 107.

The first positioning unit 101 and the second positioning unit 102 are also connected to one another, wherein the connection can be a thermal molding or the first positioning unit 101 and the second positioning unit 102 can be welded to one another. To this end the first positioning unit 101 has a first surround 108 and the second positioning unit 102 has a second surround 109. The first surround 108 and the second surround 109 here are connected to each other by thermal molding and/or are welded to one another.

In the exemplary embodiment the positioning cushion 100 has a third positioning unit 110. The third positioning unit 110 includes a stabilization unit 111. The stabilization unit 111 has a stabilization plate that imparts stability to the positioning cushion 100. Such a stabilization plate is to be understood as a plate that in normal use, for example as a support for an area of the body of the patient 17 to be examined, retains its macroscopic shape.

The positioning cushion 100 with the three positioning units 101, 102, 110 is also constructed in the form of layers. To this end the first positioning unit 101 has a first positioning layer 112 that encloses the two foam cushions 107. The second positioning unit 102 has a second positioning layer 113 that encloses the fluid cushion 103. The third positioning unit 110 has a third positioning layer 114 that encloses the stabilization unit 111. Here the third positioning unit 110, especially the third positioning layer 114 with the stabilization unit 111, is also disposed between the first positioning unit 101, especially the first positioning layer 112 with the two foam cushions 107, and the second positioning unit 102, especially the second positioning layer 113 with the fluid cushion 103.

Because of the arrangement of the stabilization plate between the first positioning unit 101, especially the first positioning layer 112 with the two foam cushions 107, and the second positioning unit 102, especially the second positioning layer 113 with the fluid cushion 103, there can be an advantageous decoupling of the first positioning unit 101 from the second positioning unit 102. In particular, for a positioning and/or fixing of for example an area of the body of the patient 17 to be examined, the positioning cushion 100 offers on both sides a soft and elastic contact surface for supporting the patient 17 because of the first positioning unit 10 and the second positioning unit 102.

The third positioning unit 110 is likewise connected to the second positioning unit 102 and the first positioning unit 101. To this end the third positioning unit 110 likewise has a third surround 115 that is connected to the second surround 109 of the second positioning unit 102 and the first surround 108 of the first positioning unit 101. The third surround 115 here is likewise connected by a thermal molding to the first surround 108 and the second surround 109 or is welded to the first surround 108 and the second surround 109.

FIGS. 6 to 9 show an alternate exemplary embodiment of the patient cushion 200. Components, features and functions that essentially remain the same are basically labeled with the same reference characters. The description given below essentially restricts itself to the differences from the exemplary embodiment in FIGS. 2 to 5, wherein in relation to components, features and functions that remain the same, the reader is referred to the description of the exemplary embodiment for FIGS. 2 to 5.

The positioning cushion 200 in FIGS. 6 to 9 has a first positioning arrangement 201 that has a foam material. In the present exemplary embodiment the first positioning arrangement 201 has a single foam cushion 202, wherein the foam cushion 202 has a recess 203 in a central area. The recess 203 comprises an elongated hole that extends in the direction of a longitudinal extent 204 of the positioning cushion 200. In an alternate embodiment of the invention the first positioning arrangement 201 can also have more than one foam cushion 202.

Figure 9:
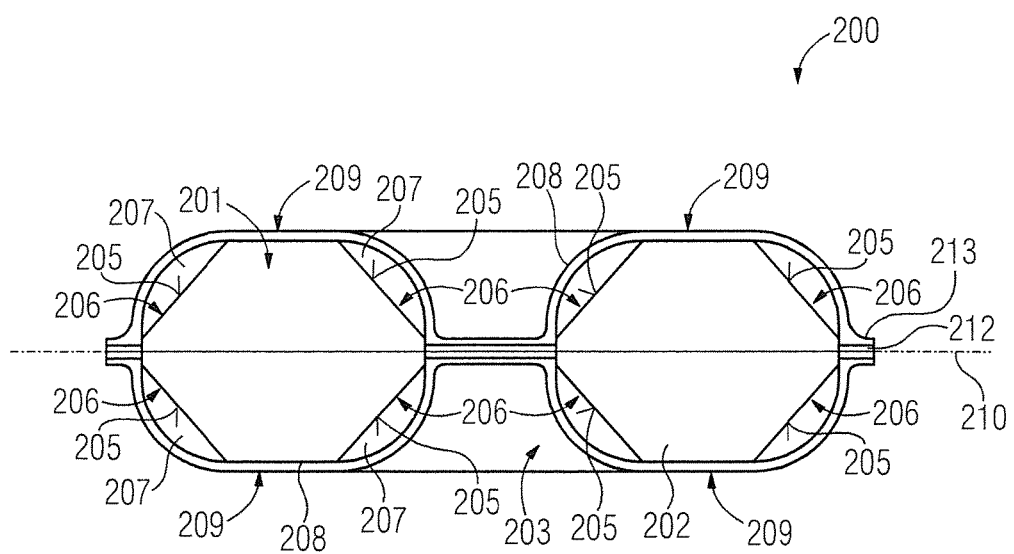
FIG. 9 shows the second exemplary embodiment of the positioning cushion, in a cross-section.

The foam cushion 202 of the first positioning arrangement 201 has sloping side surfaces 205. The side surfaces 205 are enclosed by an upper surface of the foam cushion 202 and adjoin a main extent surface of the upper surface of the foam cushion 202. The sloping side surfaces 205 of the foam cushion 202 make an obtuse angle with the main extent surface of the upper surface of the at least one foam cushion 202. The foam cushion 202 therefore has a hexagonal cross section (FIG. 9).

The positioning cushion 200 further has a second positioning arrangement 206, which encloses a number of fluid cushions 207 able to be filled with a fluid. To this end the second positioning arrangement 206 has two envelopes 208, wherein one envelope 208 envelopes and or surrounds all fluid cushions 207 that are assigned to one of the two main extent surfaces of the upper surface of the foam cushion 202. The two envelopes 208 of the second positioning arrangement 206, especially of the number of fluid cushions 207, are already pre-shaped, so that in a filled state they have a defined and/or prespecified shape. In an alternate embodiment of the invention the second positioning arrangement 206 can also have just a single fluid cushion 207 (FIG. 9).

The individual fluid cushions 207 of the second positioning arrangement 206 are disposed on the side surfaces 205 of the foam cushions 202 of the first positioning arrangement 201. Furthermore the first positioning arrangement 201, especially the foam cushion 202, has a central outer area 209 on both sides, which is disposed in each case on one side, especially of the main extent surface, of the upper surface of the foam cushion 202. The central outer area 209 encloses at least partly a central area and/or a middle area of one side, especially of the main extent surface, of the upper surface of the foam cushion 202. One of the envelopes 208 of the respective fluid cushion 207 rests in each case against one of these central outer areas. In the present exemplary embodiment one of the two envelopes 208 is each case is firmly connected to one of the two central outer areas 209 of the foam cushion 202, so that the individual fluid cushions 207, especially a boundary area between the envelopes 208 of the fluid cushion 207 and the foam cushion 202 are embodied sealed in respect of an exchange of the fluid, especially an exchange of air (FIG. 9).

Because of the arrangement of the individual fluid cushions 207 on the side surfaces 205 of the foam cushion 202 of the first positioning arrangement 201, in an emptied state of the positioning cushion 200, especially of the fluid cushion 207, a shape of the positioning cushion 200 is predetermined by the foam cushion 202. Only an area that surrounds the side surfaces 205 of the foam cushion is enlarged in the filled state by the fluid cushion 207 (FIG. 9). In an emptied state of the fluid cushion 207 the envelopes 208 rest against the side surfaces 205, so that the envelopes 208 can assume a predefined position in the emptied state. This effect is increased even further by the pre-shaped envelopes 208 of the second positioning arrangement 206.

The first positioning arrangement 201 and the second positioning arrangement 206 in such cases are disposed within the positioning cushion 200, such that the positioning cushion 200 is essentially embodied mirror-symmetrically in relation to a central plane 210. The central plane 210 preferably extends through a center of the positioning cushion 200 and is preferably parallel to the main extent surfaces of the foam cushion 202 (FIG. 9).

Figure 6:
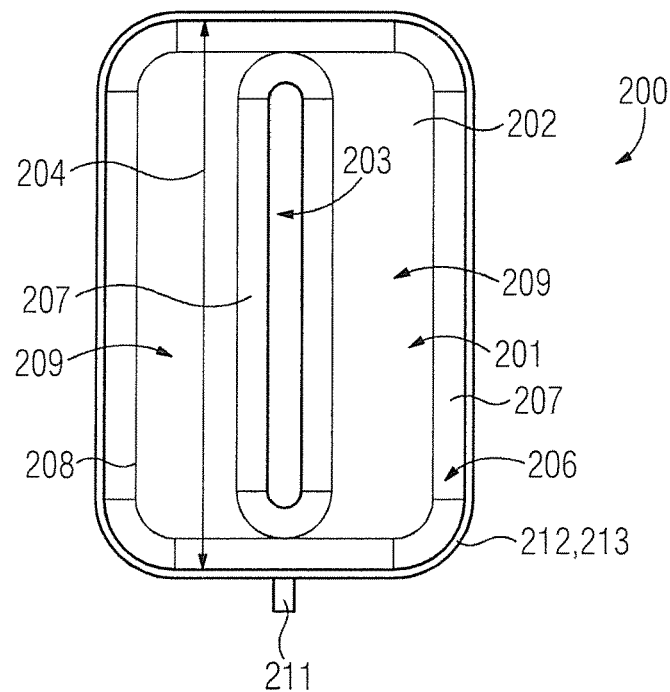
FIG. 6 shows a second exemplary embodiment of the positioning cushion, in a schematic illustration from the front.
Figure 7:
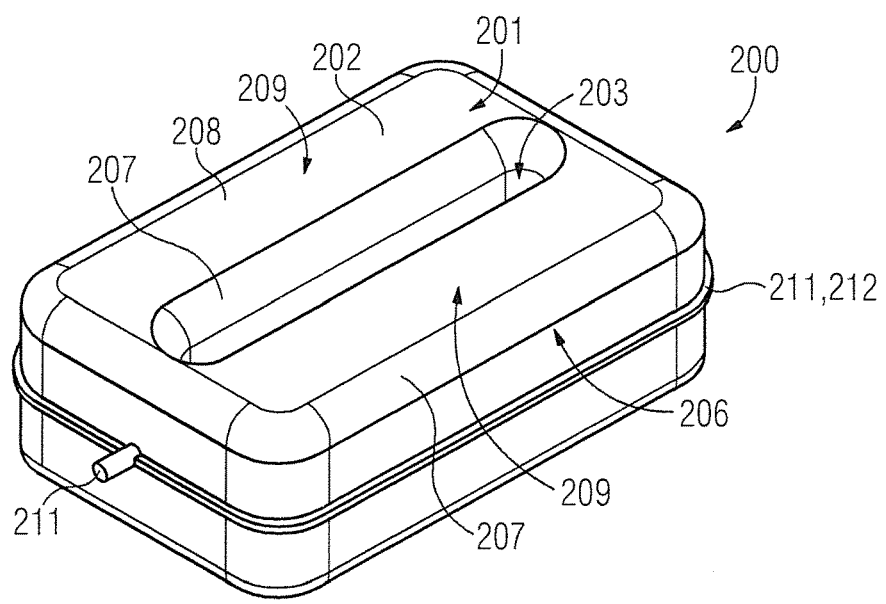
FIG. 7 shows the second exemplary embodiment of the positioning cushion, in a perspective view from the front.
Figure 8:
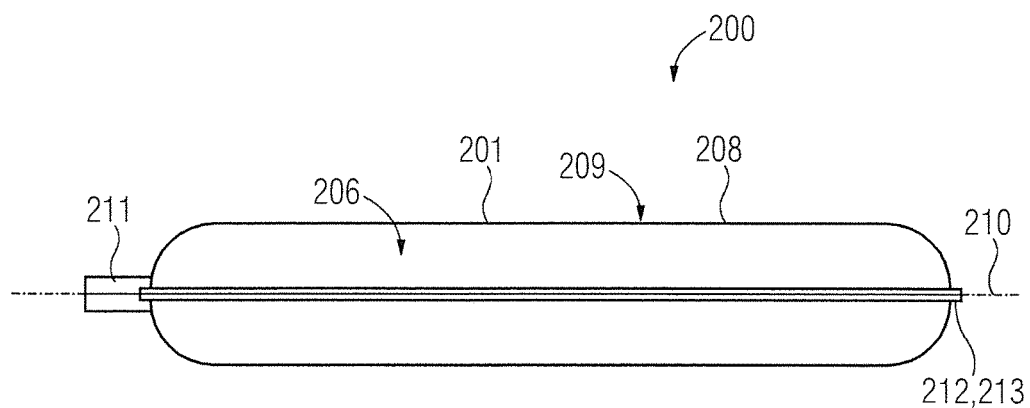
FIG. 8 shows the second exemplary embodiment of the positioning cushion, in a side view.

For filling the multiple fluid cushions 207 and/or for emptying the multiple fluid cushions 207, the second positioning arrangement 206 likewise has a valve opening 211. In the present exemplary embodiment the individual fluid cushions 207 are able to be filled with air, wherein the second positioning arrangement 206, for filling the number of fluid cushions 207 and/or for emptying the number of fluid cushions 207, has a single valve opening 211 (FIGS. 6 to 8). In an alternate embodiment of the invention the second positioning arrangement 206 can have more than a single valve opening 211.

The first positioning arrangement 201 and the second positioning arrangement 206 are also connected to one another, wherein the connection can comprise a thermal molding or the first positioning arrangement 201 and the second positioning arrangement 202 can be welded to one another. To this end the first positioning arrangement 201 has a first surround 212 and the second positioning arrangement 206 has a second surround 213. The first surround 212 and the second surround 213 here are connected to one another by means of thermal molding and/or are welded to one another. In the present exemplary embodiment the valve opening 211 is disposed on the surround 213 of the second positioning unit (FIGS. 6 to 8).

When one of the two positioning cushions 100, 200 according to FIGS. 2 to 5 or according to FIGS. 6 to 9 is used, effort for a preparation of a patient 17 is significantly simplified for medical operating personnel. In particular, for an exact positioning of the patient 17, wherein the patient 17 is to remain in this position as motionless as possible during the magnetic resonance examination, effort for the medical operating personnel can be simplified by this method. For positioning the positioning cushions 100, 200 are first positioned in an emptied state and subsequently air is pumped into the fluid cushion 103, 207 or into the number of fluid cushions 103, 207, until the positioning cushion 100, 200 assumes a final position for example, in which especially the positioning cushion 100, 200 almost completely fills a space between the area of the body of the patient 17 to be examined and an upper surface of a local radio-frequency antenna unit. After the examination the fluid cushions 103, 207 are simply emptied and an area of free movement for the patient 17, especially the area of the body of the patient 17, being examined, increases again. In this emptied state the positioning cushion 100, 200 can also be removed again from a patient positioning position.

Although modifications and changes may be suggested by those skilled in the art, it is the intention of the inventors to embody within the patent warranted hereon all changes and modifications as reasonably and properly come within the scope of their contribution to the art.

We claim as our invention:

1. A positioning cushion for positioning a subject at a positioning site, said positioning cushion comprising:
   a first positioning unit comprising a foam material;
   a second positioning unit comprising a fluid cushion having a port allowing selective filling, at said positioning site, of said fluid cushion with a fluid;
   a third positioning unit connected to each of said first and second positioning units and being situated between said first and second positioning units, said third positioning unit comprising a stabilizer that has a macroscopic shape;
   said second positioning unit comprising a deformable wall connected to said stabilizer, with said deformable wall and said stabilizer in combination forming an interior of said fluid cushion into which said fluid is received and held in order to form said fluid cushion; and
   said first second and third positioning units being adapted to receive a subject thereon to position said subject at said positioning site, with said stabilizer retaining said macroscopic shape when said subject is received thereon.

2. A positioning cushion as claimed in claim 1 wherein said port comprises a valve opening allowing selective filling and emptying of said fluid cushion.

3. A positioning cushion as claimed in claim 1 wherein said first positioning unit comprises two foam cushions, formed of said foam material, that are separate from each other.

4. A positioning cushion as claimed in claim 1 wherein said first said second position, units are connected to each other by a connection selected from the group consisting of thermal molding and welding.

5. A positioning cushion as claimed in claim 1 wherein said second positioning unit comprises a pre-shaped envelope in which said fluid cushion is situated.

6. A positioning cushion as claimed in claim 1 wherein said second positioning unit has an emptied state in which said fluid cushion contains no fluid, and wherein said second positioning unit comprises an envelope that assumes a predefined position in said emptied state.

7. A positioning cushion as claimed in claim 1 wherein said first positioning unit comprises a foam cushion formed of said foam material, said foam cushion having a recess therein.

8. A positioning cushion as claimed in claim 1 wherein said first positioning unit comprises a foam cushion formed of said foam material, said foam cushion having a sloping slide surface, and wherein at least a portion of said fluid cushion of said second positioning unit is disposed on said sloping side surface.

9. A positioning cushion as claimed in claim 8 wherein said second positioning unit comprises an envelope in which said fluid cushion is disposed, and wherein said foam cushion comprises a central exterior area and wherein said envelope rests against said central exterior area.

10. A medical imaging apparatus comprising:
    a medical data acquisition scanner;
    a patient support adapted to receive a patient thereon and to move said patient into and out of said medical data acquisition scanner;
    a positioning cushion in said patient table adapted to position said patient on said patient table, as a positioning site; and
    said positioning cushion comprising a first positioning unit comprising a foam material, a second positioning unit comprising a fluid cushion having a port allowing selective filling, at said positioning site, of said fluid cushion with a fluid, a third positioning unit connected to each of said first and second positioning units and being situated between said first and second positioning units, said third positioning unit comprising a stabilizer that has a macroscopic shape, said second positioning unit comprising a deformable wall connected to said stabilizer, with said deformable wall and said stabilizer in combination forming an interior of said fluid cushion into which said fluid is received and held in order to form said fluid cushion, and said first, second and third positioning units being adapted to receive a subject thereon to position said subject at said positioning site, with said stabilizer retaining said macroscopic shape when said subject is received thereon.

* * * * *